United States Patent [19]

Belikan et al.

[11] Patent Number: 5,158,085

[45] Date of Patent: Oct. 27, 1992

[54] LITHOTRIPSY ULTRASOUND LOCATING DEVICE

[75] Inventors: Thomas Belikan; Werner Krauss, both of Knittlingen; Helmut Wurster, Oberderdingen, all of Fed. Rep. of Germany

[73] Assignee: Richard Wolf GmbH, Knittlingen, Fed. Rep. of Germany

[21] Appl. No.: 566,587

[22] Filed: Aug. 13, 1990

[30] Foreign Application Priority Data

Sep. 29, 1989 [DE] Fed. Rep. of Germany ....... 3932516

[51] Int. Cl.$^5$ .............................................. A61B 17/22
[52] U.S. Cl. ............................ 128/660.03; 128/24 EL
[58] Field of Search ......... 128/24 EL, 24 AA, 660.03

[56] References Cited

U.S. PATENT DOCUMENTS

| | | | |
|---|---|---|---|
| 4,821,730 | 4/1989 | Wurster et al. | 128/660.03 |
| 4,896,673 | 1/1990 | Rose et al. | 128/24 EL |
| 4,915,114 | 4/1990 | Hassler | 128/24 EL |
| 4,932,414 | 6/1990 | Coleman et al. | 128/660.03 |
| 4,962,754 | 10/1990 | Okazaki | 128/660.03 |
| 4,984,575 | 1/1991 | Uchiyama et al. | 128/24 EL |
| 4,986,275 | 1/1991 | Ishida et al. | 128/660.03 |
| 4,991,604 | 2/1991 | Wurster et al. | 128/660.03 |
| 5,005,579 | 4/1991 | Wurster et al. | 128/24 EL |
| 5,005,580 | 4/1991 | Okazaki | 128/660.03 |
| 5,025,789 | 6/1991 | Hassler | 128/24 EL |
| 5,031,626 | 7/1991 | Hassler et al. | 128/24 EL |
| 5,048,527 | 9/1991 | Okazaki | 128/24 EL |
| 5,060,650 | 10/1991 | Wurster et al. | 128/24 EL |

FOREIGN PATENT DOCUMENTS

| | | |
|---|---|---|
| 2712341 | 5/1978 | Fed. Rep. of Germany . |
| 3427001 | 2/1986 | Fed. Rep. of Germany . |
| 3214789 | 10/1987 | Fed. Rep. of Germany . |

Primary Examiner—Lee S. Cohen
Assistant Examiner—K. M. Pfaffle
Attorney, Agent, or Firm—Panitch Schwarze Jacobs & Nadel

[57] ABSTRACT

A lithotripsy ultrasound locating device comprises at least one locating transducer having a plurality of focal ranges and which is associated with a therapy transducer and is axially adjustable in relation to its focus; a position indicator which generates a signal representing the distance between the sound head of the locating transducer and the focus of the therapy transducer; a computer; a monitor on which a target mark representing the focus of the therapy transducer is displayed; and an electronic transmitter/receiver arrangement controlled by the computer in order to produce an image of a concretion to be destroyed which image is constantly optimal. The computer controls, as a function of the signal emitted by the position indicator and by way of the transmitter/receiver arrangement, the focal range of the locating transducer which, at the given distance at that moment between the sound head and the focus of the therapy transducer always lies in the range thereof. The computer further generates a signal following up the target mark on the monitor according to the signal emitted by the position indicator. The following-up signal is passed to the monitor so that, where applicable, in each axial position of the locating transducer, the image of the concretion displayed by the monitor lies in the target mark.

6 Claims, 1 Drawing Sheet

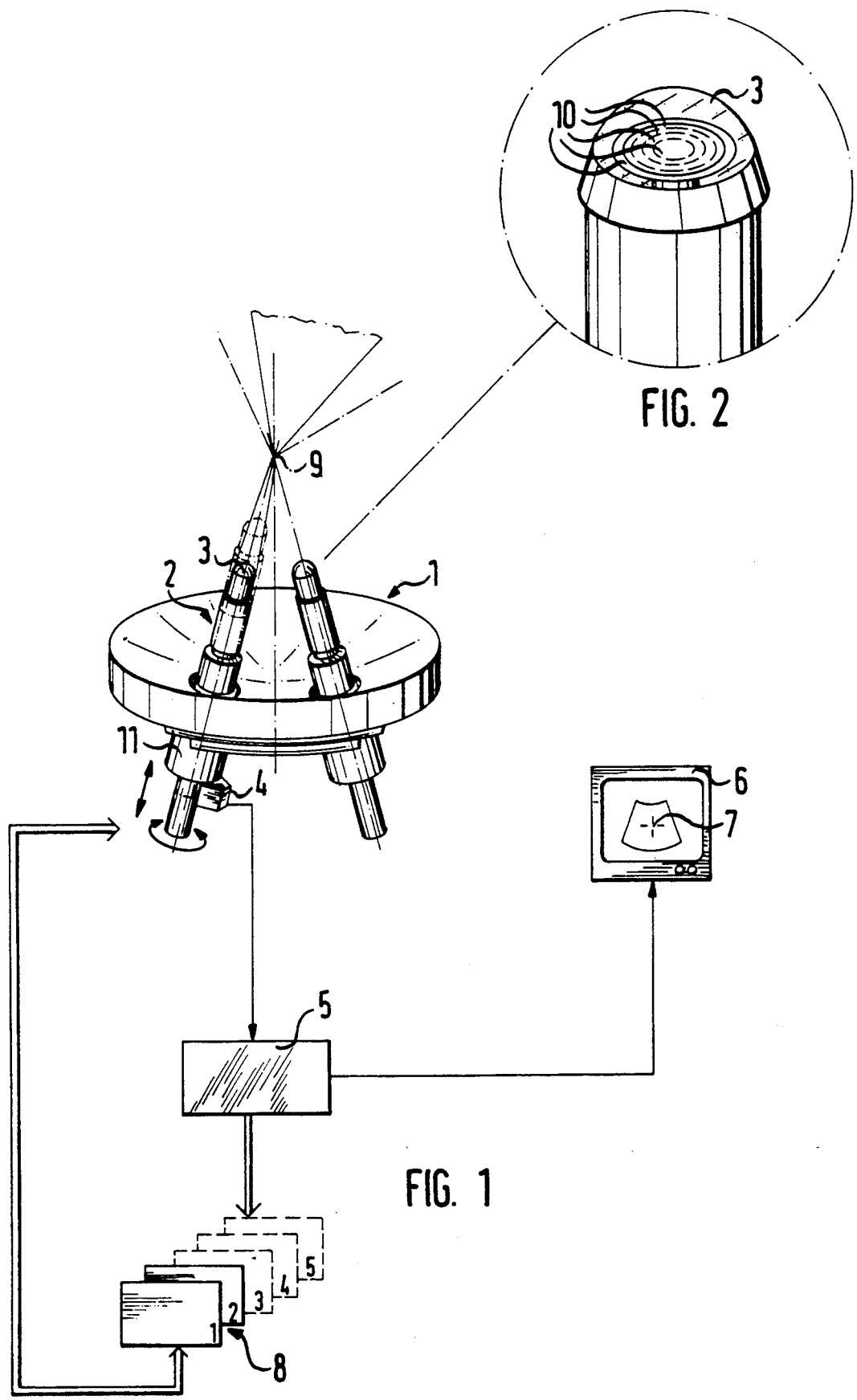

LITHOTRIPSY ULTRASOUND LOCATING DEVICE

FIELD OF THE INVENTION

The invention relates to a lithotripsy ultrasound locating device, comprising, at least one locating transducer having several focal ranges, which is associated with a therapy transducer for emitting ultrasound shock waves, and is axially adjustable with respect to the focus of the therapy transducer; a position indicator for generating a signal representing the distance between the sound head of the locating transducer and the focus of the therapy transducer, a computer; a monitor for portraying a target mark representing said focus; and an electronic transmitter/receiver arrangement controlled by the computer.

BACKGROUND OF THE INVENTION

In such a sound locating device the monitor portrays a body concretion which is to be destroyed, as far as possible in such a way as to provide sufficient information as to the position, size and condition of the concretion to allow the doctor carrying out the treatment to determine the nature and duration of the ultrasound shock waves which are to be applied in order to destroy the concretion.

When the target mark on the monitor is thereby located on the image of the concretion, the focus of the therapy transducer, and the concretion are coincident, so that the ultrasound shock waves can then be applied thereto.

Basically, it is advantageous for the sound head of the locating transducer, which is for example a B-scanner, to be brought as far as possible against the skin of the patient, in order to avoid reflection and multiple echoing of the ultrasound waves emitted by the sound head, thereby to obtain as clear an image of the concretion as possible. Where in any desired position of the locating transducer, the concretion, is, by reason of said multiple echoes or reflections, only portrayed indistinctly on the monitor, a locating transducer can be displaced in the direction of the focus of the therapy transducer, thereby to obtain a clearer image of the concretion. In this case, with the application of a simple B-scanner, the concretion is displaced from the focal range of the locating transducer, that is to say the image resolution decreases. In practice, a locating transducer having several focal ranges can be used. As a function of the distance of the sound head of the locating transducer, from the focus of the therapy transducer the focal range of the locating transducer can be selected by the operation of an actuating element, in which focal range the concretion is located at that time, in order to provide the best possible image resolution.

With the patient positioned on a treatment table, the locating transducer can be moved against the patient's skin (and hence in the direction of the focus of the therapy transducer). By manual operation of the actuating element, empirically the most suitable focal range can be selected in order to achieve as good an image resolution as possible. It is to be noted in this regard that concretions may be located at differing distances from the surface of the patient's skin. Thus, for example, a stone in the ureter lies relatively deep in the patient's body, whereas other stones lie nearer to the surface of the skin.

SUMMARY OF INVENTION

It is, therefore, an object of the present invention to provide for the best possible image of a concretion to be destroyed, to be displayed on the monitor without the need for external adjustment, the target mark on the monitor being always coincident with the image of said concretion, when the focus of the therapy transducer is aligned with the concretion; independently of the axial adjustments of the locating transducer.

According to the present invention, therefore, the computer controls, as a function of the signal generated by the position indicator and by way of the electronic transmitter/receiver arrangement, the focal range of the ultrasound locating transducer which at the given distance at that moment of the sound head from the focus of the therapy transducer always lies in the range thereof. The computer passes to the monitor a signal following up the target mark on the monitor corresponding to said signal generated by the position indicator.

The position indicator may, for example, be fixedly arranged on a gear unit, by means of which said locating transducer is axially adjustable. The position indicator generates a signal which represents the respective distance between the sound head of said locating transducer and the focus of the therapy transducer. This signal is passed to the computer. By virtue of the fixed relationship of the ultrasound locating transducer with respect to the therapy transducer, and thus with respect to its focus, the computer can determine which focal range of the ultrasound locating transducer lies in the range of the concretion to be portrayed. The computer accordingly, generates an output signal which is passed to the electronic transmitter/receiver arrangement, which in turn controls the active and passive ranges of the locating transducer, which ranges correspond to the selected focal range. The computer additionally generates a further signal which follows up the target mark on the monitor according to the signal emitted by the position indicator and thus according to the distance at that moment between the sound head of the ultrasound locating transducer and the focus of the therapy transducer.

The sound head of the locating transducer may comprise at least two crystal rings, the sound head thus having at least two focal ranges. Such a locating transducer operates according to the so-called "Annular-Phased-Array" principle. Sound heads of this kind have the advantage, as compared, for example, with "Linear-Phased-Array" sound heads, that they radiate a symmetrical sound lobe. In use of "Linear-Phased-Array" sound heads, the sound field cannot be controlled electronically transversely of the sectional plane. "Annular-Phased-Array" sound heads, however, can also detect thin layers vertically with respect to the sectional plane, because the sound beam is formed so as to be circularly symmetrical. The locating transducer is preferably mounted so as to be rotatable about its main axis. The concretion can thereby be represented on the monitor from various image planes, so that the informative content of the image is increased.

The therapy transducer is preferably a cap-shaped transducer, the locating transducer(s) being arranged in the interior of the cap, a simple fixed relationship between the locating transducer and the focus of the therapy transducer being thereby achieved.

It will be appreciated in the light of the foregoing, that the ultrasound locating device, automatically provides the best possible image of the concretion on the monitor. If the locating transducer is brought closer to the focus of the therapy transducer that is to say closer to the patient's skin, the focal range of the sound head is switched over so as to be optimal, and the target mark is followed up on the monitor so that the concretion is, where applicable, represented as being located in the focus of the therapy transducer.

BRIEF DESCRIPTION OF THE DRAWINGS

FIG. 1 is a diagrammatic, isometric view shown partly in schematic form, of a lithotripsy ultrasound locating device, in which two locating transducers are arranged in therapy transducer cap; and FIG. 2 is an enlarged view of a sound head of one of the ultrasound locating transducers.

DETAILED DESCRIPTION OF THE INVENTION

As shown in FIG. 1, two locating transducers 2 are fixedly arranged in the cap of a therapy transducer 1, so as to be axially adjustable by means of a drive 11 with respect to the focus 9 of the therapy transducer 1, as indicated by the double arrow in FIG. 1. Also the locating transducers 2 are mounted to the cap so as to be rotatable about their longitudinal axes.

A position indicator 4 is connected to the drive 11 for the locating the left hand (as seen in FIG. 1) transducer 2. The position indicator 4 may consist, for example, of a precision potentiometer, or of a digital absolute value indicator. In either case, the position indicator 4 generates a signal representing the distance between the sound head 3 and the focus 9 of the therapy transducer 1. The clarity of the signal so generated arises from the fixed association of the locating transducer 2 with respect to the therapy transducer 1.

The signal emitted by the position indicator 4 is passed to a computer 5 for further processing thereby.

Firstly, the computer 5 generates a control signal which is passed to an electronic transmitter/receiver arrangement 8, shown diagrammatically in FIG. 1 as consisting of five planes. On the basis of the signal generated by the position indicator 4, the computer 5 "recognises" the distance by which the sound head 3 is spaced from the focus 9 of the therapy transducer 1, and accordingly, controls the corresponding plane of said arrangement 8.

The transmitter/receiver arrangement 8 has, in practice, as many planes as the sound head 3 has crystal rings 10 (FIG. 2). The crystal rings 10 in the sound head 3 operate according to the Annular-Phased-Array principle.

Secondly, the computer 5 generates a signal which follows up a target cross 7 on a monitor 6 according to the signal emitted by the position indicator 4 and thus according to the distance at that moment of the sound head 3 from the focus 9 of the therapy transducer 1.

Starting from the position where a concretion in a patient's body, which is the concretion to be destroyed, has been roughly located, and the focus 9 is aligned with the concretion, the locating transducer 2 is brought against the patient's skin (for the reasons set forth above), that is to say the transducer 2 is moved in the direction of the focus 9. The said compensation by the follow-up signal generated by the computer 5 for the target cross 7 provides for the latter always to be located on the image of the concretion, in so far as the latter actually remains in the focus 9 of the therapy transducer 1. The follow-up signal from the computer 5 is passed in known manner to the deflection devices of the monitor 6.

What is claimed is:

1. A lithotripsy ultrasound locating device comprising:
    a therapy transducer for emitting ultrasound shock waves and having a focus and a range of focus;
    at least one locating transducer associated with the therapy transducer, said locating transducer having a sound head means for providing a plurality of focal ranges and being axially adjustable with respect to said focus of the therapy transducer;
    a position indicator for generating a first signal representing the distance between said sound head means and said focus;
    a computer;
    a monitor for portraying thereon a target mark representing said focus; and
    an electronic transmitter/receiver arrangement controlled by the computer; wherein the computer includes means for selecting, as a function of the first signal generated by the position indicator and by way of said transmitter/receiver arrangement, one of said focal ranges of the locating transducer so that in respect of a momentary given distance between the sound head means and said focus of the therapy transducer, the selected focal range lies within the range of focus of the therapy transducer, and wherein the computer passes to the monitor a second signal following up the target mark on the monitor in accordance with the first signal generated by the position indicator.

2. A locating device as claimed in claim 1, wherein the sound head means of the locating transducer comprises at least two crystal rings.

3. A locating device as claimed in claim 2, wherein the locating transducer is mounted for rotation about the main axis of the locating transducer.

4. A locating device as claimed in claim 1 wherein the locating transducer is mounted for rotation about the main axis of the locating transducer.

5. A locating device as claimed in claim 1, wherein the therapy transducer is cap-shaped and the locating transducer is arranged within the cap-shaped transducer.

6. A locating device as claimed in claim 1 wherein the sound head means of the locating transducer comprises an annular-phased-array transducer.

* * * * *